United States Patent [19]

Fougnot et al.

[11] Patent Number: 4,945,054

[45] Date of Patent: Jul. 31, 1990

[54] PROCESS FOR THE SEPARATION AND PURIFICATION OF PROTEASES AND ANTIPROTEASES OF BLOOD CLOTTING, AS WELL AS OF THE PROTEASE/ANTIPROTEASE COMPLEX

[75] Inventors: Christine Fougnot, Saint Denis; Marcel Jozefowicz, Lamorlaye, both of France; Robert D. Rosenberg, Brookline, Mass.

[73] Assignee: Commissariat a l'Energie Atomique, Paris, France

[21] Appl. No.: 495,511

[22] Filed: May 17, 1983

[30] Foreign Application Priority Data

May 19, 1982 [FR] France .................. 82 08779

[51] Int. Cl.$^5$ .................. C12N 9/74; C12N 9/48
[52] U.S. Cl. .................. 435/214; 435/212; 530/380; 530/393; 530/412; 530/416
[58] Field of Search .................. 435/4, 7, 13, 23, 174, 435/180, 181, 184, 214, 814, 815; 436/63, 69, 86, 181; 210/673, 692

[56] References Cited

U.S. PATENT DOCUMENTS

| | | | |
|---|---|---|---|
| 3,531,463 | 9/1970 | Gustafson et al. | 210/692 X |
| 3,902,964 | 9/1975 | Greenspan | 435/296 |
| 3,928,587 | 12/1975 | Sawyer | 435/230 |

FOREIGN PATENT DOCUMENTS

| | | |
|---|---|---|
| 12195D/08 | 2/1981 | European Pat. Off. |
| 0011088 | 1/1979 | Japan .................. 210/692 |

OTHER PUBLICATIONS

Fougnot, C. et al., *Thrombosis Research*, vol. 28, pp. 37–46, Oct. 1982.

Vesa, V. et al. (Uses, Nauchno-Issled, Inst. Prikl, Enzimol., Vilnius, USSR). Polifermentn. Sist., Tezisy. Soobshch. Uses.

Semin, "Perspekt. Primem. Polifermentn. Sist. Nar. Khoz." 1980, 1, 52–80, (Edited Klesov. A. A.)–English Translation.

Walsh et al., Methods in Enzymology, vol. XIX, (Eds Perlmann & Lorand) pp. 31–33, 1970.

Norde et al., *J. Colloid and Interface Sci.*, vol. 66, No. 2, pp. 257–284, 1978.

Vesa, V. et al., Chem Abst. vol. 95: 92840m, 1981.

Norde et al., Chem Abst. vol. 89: 210631v, 1978.

Norde et al., Chem Abst. vol 89:210632w, 1978.

Norde et al., Chem., Abst., vol. 89: 210633x, 1978.

Norde et al., Chem., Abst., vol. 89: 210634y, 1978.

*Primary Examiner*—Robin L. Teskin
*Assistant Examiner*—Larry Millstein
*Attorney, Agent, or Firm*—Weiser & Stapler

[57] ABSTRACT

The present invention relates to a process for separating and purifying proteases and antiproteases. This process is characterized in that there are placed in contact an insoluble cross-linked polymer including in its chain the group —$SO_3R_1$— and/or the group —$SO_2R_2$— in which $R_1$ denotes a hydrogen atom or metal and $R_2$ denotes the remainder of an amino acid linked to the —$SO_2$— bridge through its amine —NH—, function, with the solution containing proteases and antiproteases or their complex; separating the polymer which has absorbed the desired protein, washing it carefully with the buffer, desorbing the absorbed protein by a solution of a polycationic compound in the case of T or by an albumin solution in the case of AT or of the complex T-AT, and isolating the protein, if desired, by known means, such as, especially, freeze drying. The invention is useful for studying the mechanism of blood coagulation.

12 Claims, No Drawings

PROCESS FOR THE SEPARATION AND PURIFICATION OF PROTEASES AND ANTIPROTEASES OF BLOOD CLOTTING, AS WELL AS OF THE PROTEASE/ANTIPROTEASE COMPLEX

BACKGROUND OF THE INVENTION

The present invention relates to a novel process for separating and purifying proteases and antiproteases of blood clotting (and particularly thrombin (T) and antithrombin (AT)) as well as the thrombin-antithrombin complex T-AT.

The study and knowledge of the mechanisms of blood clotting nescessitates having available large amounts of thrombin and antithrombin in the pure state.

Applicants, who have acquired great experience in the preparation of polymers endowed with anticoagulant properties (cf. particularly the French patent 2 461 724 or ANN. BIOMED. ENG. 1979), have established laws of affinity between these polymers and certain proteins such as proteases and antiproteases of blood coagulation. It was an object to provide a process of separation and purification of proteases and of antiproteases (such as T and AT) which is simple, economical and of great reliability.

GENERAL DESCRIPTION OF THE INVENTION

According to the present invention there is provided a process for the separation and purification of proteases (T) and of antiproteases (AT) of blood coagulation as well as of their complex (T-AT), the said process comprising of contacting a insoluble cross-linked polymer including in its chain the $-SO_3R_1-$ group and/or the $-SO_2R_2-$ group in which $R_1$ denotes a hydrogen atom or metal and $R_2$ denotes the rest of an amino acid linked to the $-SO_2-$ bridge through its amine function $-NH-$, with a solution containing proteases or antiproteases or their complex, separating the polymer which has absorbed the desired protein, washing it carefully with a buffer, desorbing the absorbed protein by a solution of polycationic compound in the case of T or by an albumin solution in the case of AT or of the complex T-AT, and isolating the protein if desired, by known means such as lyphilisation, especially.

According to an advantageous embodiment of to the invention, the cross-linked polymer is polystyrene.

According to another advantageous embodiment of the invention, the polymer before its contacting with the solutions containing the proteins is equilibrated to a pH comprised between 7.3 and 7.5 by successive washings with a suitable buffer.

According to the invention, the insoluble cross-linked polymer employed is in the proportion comprised between 50 and 2500 mg per mg of protein present and, preferably, between 50 and 80 mg per 1 mg of T, between 200 and 2000 mg per 1 mg of AT and between 220 and 2000 mg per 1 mg of the T-AT complex.

In an advantageous embodiment according to the invention, the polycationic compound is taken from the group which comprises hexadimethrine bromide and polylysine, and the amount of this compound employed comprises between 10 and 15 mg per mg of protein.

In another advantageous embodiment according to the invention, the amount of albumin employed for the desorption is comprised between 750 and 2500 mg per mg of the desired protein absorbed, and preferably, between 800 and 1200 mg per 1 mg of AT, and between 100 and 2000 mg per 1 mg of the complex T-AT.

In accordance with the invention, the buffer used for the equilibration of the polymer before absorption and for the washing after absorption is taken from the group which comprises the Michaelis buffer and the Tris buffer.

Besides the foregoing features, the invention comprises other features which will emerge from the description which follows, which refers to examples of the employment of the process according to the present invention.

It must be understood however, that these examples are given purely by way of illustration of the invention, of which they do not constitute in any way a limitation thereof.

EXAMPLES OF SEPARATION

EXAMPLE 1

Separation of thrombin 1 g of polymer according to the invention is previously equilibrated to pH 7.4 by several successive washings with the Tris buffer. Then the polymer is washed for a half hour at 4° C. with a solution containing 18.75 mg of thrombin. At the end of this time, the polymer is separated (either by centrifugation, or on sintered glass), and it is washed by 5 times its volume of the same buffer. Then the polymer is mixed (for a half hour at 4° C.) with 10 ml of a solution with 10 mg/ml of hexadimethrin bromide. The polymer complexed with hexadimethrin bromide is then separated from the solution containing the desorbed thrombin. The latter is isolated by lyophilisation. 15 mg of thrombin are obtained, namely a yield of 80%.

EXAMPLE 2

Separation of antithrombin 10 g of polymer are previously equilibrated to pH 7.4 by several successive washings with Michaelis buffer. The polymer is then mixed with 30 ml of plasma for one half hour at 4° C. The gel is then separated from the plasma by centrifugation (or filtration on sintered glass). The polymer is then washed with 5 times its volume of Michaelis buffer, then mixed for a half hour at 4° C. with 30 ml of the same buffer containing 100 mg/ml of albumin (bovine or human). The residual solution containing the desorbed antithrombin and the excess albumin is then recovered by filtration (or centrifugation). It is then injected onto a heparin-sepharose column to separate the two proteins. 3 mg of antithrombin are obtained, namely a yield of 60%.

EXAMPLE 3

Separation of antithrombin on a column

The separating column is prepared with a polymer previously swollen and equilibrated in Tris buffer. The plasma is then passed over the polymer gel. The unabsorbed plasma is eluted by washing with the buffer. Then onto the column is passed a solution with 100 mg/ml of albumin and the solution containing the antithrombin and the excess albumin is recovered. This solution is then passed onto heparin-sepharose indicated in Example 2.

3 mg of antithrombin are obtained. Yield: 60%.

EXAMPLE 4

Separation of the T-AT 10 g of polymer are previously equilibrated to pH 7.4 by several successive washings with Tris buffer. The polymer is then mixed with 30 ml of plasma containing the thrombin-antithrombin complex in a proportion of 300 nMoles/liter. After one half hour at 4° C., the polymer is separated from the plasma by centrifugation. The polymer is then washed with 5 times its volume of the buffer, then with 5 volumes of the same buffer containing 100 mg/ml of albumin for one half hour at 4° C. The polymer is then introduced into a column and the T-AT complex is eluted by buffer containing 250 mg/ml of albumin, until total elution (the measurement is carried out by a specific radio-immuno test). The complex is separated from the albumin by passage of the eluate over a column of Concanavaline A-sepharose (or heparin-sepharose). 15 mg of the complex are recovered, namely a yield of about 50%.

As emerges from the foregoing, the invention is in no way limited to those of its types of application, embodiments and uses which have just been described more explicitly; it encompasses on the contrary all modifications thereof which may come to the spirit of the technician skilled in the art, without departing from the framework, nor the scope of the present invention.

What is claimed is:

1. A process for the separation and purification of a protein selected from the group consisting of thrombin (T), antithrombin (AT) and the complex thrombin-antithrombin (T-AT) from a solution which process consists essentially of contacting an insoluble cross-linked polymer including in its chain at least one member of the group consisting of $-SO_3R_1-$ and $-SO_2R_2-$, in which $R_1$ hydrogen or a metal, and $R_2$ is an amino acid residue linked to the $-SO_2-$ bridge through its amine function $-NH-$, with a solution containing protein selected from the group consisting of (T), (AT) and (T-AT), separating the polymer which has absorbed one of the said proteins from said solution, washing the polymer on which desired protein is absorbed with a buffer, desorbing (a) the absorbed protein (T) with a solution of a polycationic compound, or (b) the absorbed (AT) or (T-AT) with an albumin solution and isolating (T), (AT) or (T-AT), respectively.

2. The process of claim 1, wherein T is isolated.
3. The process of claim 1 wherein AT is isolated.
4. The process of claim 1 wherein T-AT is isolated.
5. The process of claim 1 wherein the cross-linked polymer is polystyrene.
6. The process of claim 5 wherein the polymer is equilibrated to a pH between about 7.3 and about 7.5 by washing with a buffer before contacting the polymer with the protein solution.
7. The process of claim 1 wherein the insoluble, cross-linked polymer is in an amount between 50 and 2500 mg per mg of protein.
8. The process of claim 7 wherein the amount of polymer is between 50 and 80 mg per 1 mg of (T), between 200 and 2000 mg per 1 mg of (AT) and between 220 and 2000 mg per 1 mg of (T-AT).
9. The process of claim 1 wherein the polycationic compound is selected from the group consisting of hexadimethrine bromide and polylysine in an amount between 10 and 15 mg per 1 mg of (T).
10. The process of claim 1 wherein the amount of albumin used for desorption is between 750 and 2500 mg per 1 mg of (AT) or (T-AT) absorbed.
11. The process of claim 1 wherein the amount of albumin is between 800 and 1200 mg per 1 mg of (AT) and between 100 and 2000 mg per 1 mg of (T-AT).
12. The process of claim 1 wherein the buffer is selected from the group consisting of Michaelis buffer and Tris buffer.

* * * * *